US011504279B2

(12) United States Patent
Ng et al.

(10) Patent No.: US 11,504,279 B2
(45) Date of Patent: Nov. 22, 2022

(54) METHOD AND DEVICES FOR INCISION AND INSERTION OF A VENTILATION TUBE

(71) Applicant: National University of Singapore, Singapore (SG)

(72) Inventors: Cailin Ng, Singapore (SG); Wenyu Liang, Singapore (SG); Kok Kiong Tan, Singapore (SG); Chee Wee Gan, Singapore (SG); Lynne Hsueh Yee Lim, Singapore (SG)

(73) Assignee: National University of Singapore, Singapore (SG)

( * ) Notice: Subject to any disclaimer, the term of this patent is extended or adjusted under 35 U.S.C. 154(b) by 370 days.

(21) Appl. No.: 16/647,185

(22) PCT Filed: Sep. 13, 2018

(86) PCT No.: PCT/SG2018/050470
§ 371 (c)(1),
(2) Date: Mar. 13, 2020

(87) PCT Pub. No.: WO2019/054946
PCT Pub. Date: Mar. 21, 2019

(65) Prior Publication Data
US 2021/0161718 A1 Jun. 3, 2021

(30) Foreign Application Priority Data

Sep. 13, 2017 (SG) .............................. 10201707514T

(51) Int. Cl.
*A61F 11/20* (2022.01)
(52) U.S. Cl.
CPC ................................. *A61F 11/202* (2022.01)
(58) Field of Classification Search
CPC ............... A61F 11/202; A61B 17/3209; A61B 17/3468
See application file for complete search history.

(56) References Cited

U.S. PATENT DOCUMENTS

2008/0058831 A1 3/2008 Fujiwara
2009/0299379 A1 12/2009 Katz et al.
(Continued)

FOREIGN PATENT DOCUMENTS

CN 2034442 U 3/1989
CN 102014795 A 4/2011
(Continued)

OTHER PUBLICATIONS

International Search Report and Written Opinion for Application No. PCT/SG2018/050470 dated Nov. 16, 2018 (9 pages).
(Continued)

*Primary Examiner* — Richard G Louis
(74) *Attorney, Agent, or Firm* — Michael Best & Friedrich LLP

(57) ABSTRACT

Disclosed is a device for incision and insertion of a ventilation tube during myringotomy, comprising a cutter member configured to make an incision; a holder member configured to dispose the ventilation tube in an orientation in which a longitudinal axis of the ventilation tube is substantially perpendicular to the cutter member; and a pusher member configured to apply a pushing force to a first end of the ventilation tube in a direction substantially perpendicular to the longitudinal axis, the first end of the ventilation tube being disposed closer to the cutter member than a second end of the ventilation tube; wherein the holder member comprises a pivot element configured to releasably engage the second end of the ventilation tube such that the ventilation tube is pivotable under the pushing force applied to the first end of the ventilation tube by the pusher member, for insertion of the first end of the ventilation tube into the incision.

21 Claims, 15 Drawing Sheets

(56) References Cited

U.S. PATENT DOCUMENTS

2013/0338678 A1    12/2013  Loushin et al.
2015/0164695 A1    6/2015  Liu et al.
2016/0045370 A1    2/2016  Andreas

FOREIGN PATENT DOCUMENTS

| | | |
|---|---|---|
| CN | 203898547 U | 10/2014 |
| CN | 104519843 A | 4/2015 |
| CN | 104958133 A | 10/2015 |
| CN | 106999301 A | 8/2017 |
| JP | 2016511664 A | 4/2016 |
| WO | 2013188338 A1 | 12/2013 |
| WO | 2014042592 A1 | 3/2014 |

OTHER PUBLICATIONS

Ng et al., "Novel design and validation of a micro instrument in an ear grommet insertion device," J. Med. Devices, 2018, 12(3):031004.
Chinese Office Action for Application No. 201880055302.5 dated Dec. 16, 2021 (8 pages).

(a)

(b)

METHOD AND DEVICES FOR INCISION AND INSERTION OF A VENTILATION TUBE

CROSS REFERENCE TO RELATED APPLICATIONS

This application is a national stage filing under 35 U.S.C. § 371 of International Patent Application No.: PCT/SG2018/050470, filed Sep. 13, 2018, which claims priority to Singapore Patent Application No. 10201707514T, filed Sep. 13, 2017, the entire contents of all of which are hereby incorporated by reference herein.

FIELD OF INVENTION

The present invention relates broadly to method and devices for incision and insertion of a ventilation tube.

BACKGROUND

Any mention and/or discussion of prior art throughout the specification should not be considered, in any way, as an admission that this prior art is well known or forms part of common general knowledge in the field.

Otitis media with effusion (OME) is a very common ear disease that causes body imbalance, discomfort and may even result in irreversible damage to the middle ear structure. When medication as a treatment for OME fails, a ventilation tube (VT, or grommet) is surgically inserted on the tympanic membrane (TM) so that the accumulated fluid can be drained out. The procedure is called "myringotomy with tube insertion". It starts by performing a myringotomy, which involves making a small incision on the TM, and then inserting a VT into the incision. This surgery can be performed under local anaesthesia (LA) in adults if they can tolerate the discomfort, but the usual practice for young children is to use general anaesthesia (GA) as the pain tolerance level of young children is very low. Approximately 90% of children have OME at some time before school age, and the insertion of VT is one of the most common paediatric surgeries performed, and the most common reason for a child to undergo a GA. Studies have shown that there are long term health effects from GA, including possible delay in brain development of children. Hence there is a need to research on ways to avoid GA during myringotomy and VT insertion. One possible way is to shorten the duration of the incision and VT insertion procedures such that it is over in a blink of an eye and the child only has to be still for a short while. In this case, a mild sedation or local anaesthesia may preferably be sufficient.

There have been several developments that aim to do achieve that goal, by combining the 2-step procedures into a single step. This can eliminate the need to change tool sets hence shorten the duration. Two such examples are the "Insertion System for Deploying a Ventilation Device" by Perceptis Medical Inc (US 2013/0338678) and the "Tympanic Membrane Pressure Equalization Tube Delivery System" by Acclarent Inc (US 2015/0164695). Both systems utilise a cutting sheath or cutting member to incise the TM and a deformable VT that is preloaded within the sheath or shaft such that when the VT is inserted into the incision, and the shield or sheath that is holding the VT is released, the distal flange of the deformable VT opens up and assumes an expanded configuration. In both systems, the deformable VT is custom made by the respective companies. This means that users of the systems have to use the companies specific VTs, and would be constrained to the specific VT's shape, size and material. This is undesirable as different patients require different VTs according to their age and the severity of OME.

In light of the above, it would be desirable to provide an alternative device that not only provides a system that facilitates the VT insertion without requiring a 2-step process or multiple tool set changes, but would also allow the use of commercially available VTs of differing sizes and shapes. Also, for neonate and infants, the TM is in an extremely oblique position, whereas for adults, the TM angles range from 45 degrees to 60 degrees. Hence, it would be desirable for the system to be able to cater to a wide-range of TM angles.

Embodiments of the present invention seek to address at least one of the above needs.

SUMMARY

In accordance with a first aspect of the present invention, there is provided a device for incision and insertion of a ventilation tube, the device comprising a cutter member configured to make an incision; a holder member configured to dispose the ventilation tube in an orientation in which a longitudinal axis of the ventilation tube is substantially perpendicular to the cutter element; and a pusher member configured to apply a pushing force to a first end of the ventilation tube in a direction substantially perpendicular to the longitudinal axis, the first end of the ventilation tube being disposed closer to the blade than a second end of the ventilation tube; wherein the holder member comprises a pivot element configured to releasably engage the second end of the ventilation tube such that the ventilation tube is pivotable about the pivot element under the pushing force applied to the first end of the ventilation tube by the pusher member, for insertion of the first end of the ventilation tube into the incision.

In accordance with a second aspect of the present invention, there is provided use of the device of the first aspect in making an incision and inserting a ventilation tube in a membrane.

In accordance with a third aspect of the present invention, there is provided a method for making and incision and inserting a ventilation tube in a membrane, the method comprising the steps of making an incision using a cutter member; disposing the ventilation tube in an orientation in which a longitudinal axis of the ventilation tube is substantially perpendicular to the cutter element using a holder member coupled to the cutter member; applying a pushing force to a first end of the ventilation tube in a direction substantially perpendicular to the longitudinal axis, the first end of the ventilation tube being disposed closer to the blade than a second end of the ventilation tube, using a pusher element coupled to the cutter member and the holder member; releasably engaging the second end of the ventilation tube using a pivot element of the holder element; and pivoting the ventilation tube about the pivot element using the pushing force applied to the first end of the ventilation tube by the pusher member, for inserting the first end of the ventilation tube into the incision.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Embodiments of the present invention provide a method and device for incising the TM or any other membrane and inserting a commercially available VT or any equivalent tube into the membrane in a smooth and continuous motion without requiring a change of tool sets.

Figure 1:
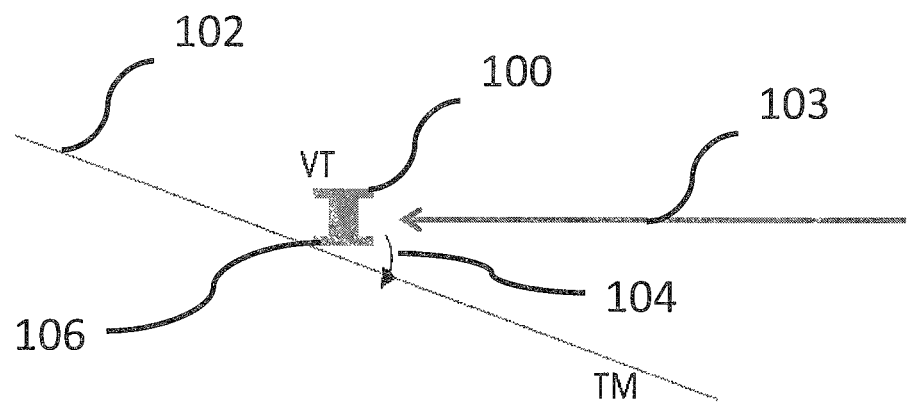
FIG. 1 shows a schematic drawing illustrating upright position of VT against a very oblique TM, with only a slight rotation needed for insertion, according to example embodiments.

The method according to example embodiments includes to first make an incision that is around the width of the VT to be inserted. Then, the VT is placed in an upright position that is perpendicular to the incision, such that the edge of the inner flange is facing the incision. With a rotating motion, the inner flange is tilted into the incision, while the outer flange is pulled slightly outwards to facilitate the rotation. In this way, the VT will be eased into the incision by using a pushing force (at the bottom) and pulling force (at the top) that creates a torque. By using this method, the entire insertion procedure can advantageously be completed in under one second according to example embodiments, and there is minimal trauma to the TM during VT insertion. Also, the method according to example embodiments can allow surgeons to be able to cater to a larger range of TM angles such that patients with very oblique TM down to 20 degrees will be able to use this system, and it is especially effective for oblique TM. This is because the VT 100 will approach the TM 102 in an upright direction along an approach direction 103 according to example embodiments, and only a slight rotational motion 104 is required to insert the inner flange 106 of the VT 100 into the TM 102 if the TM 102 is oblique, as shown in FIG. 1.

Figure 2A:
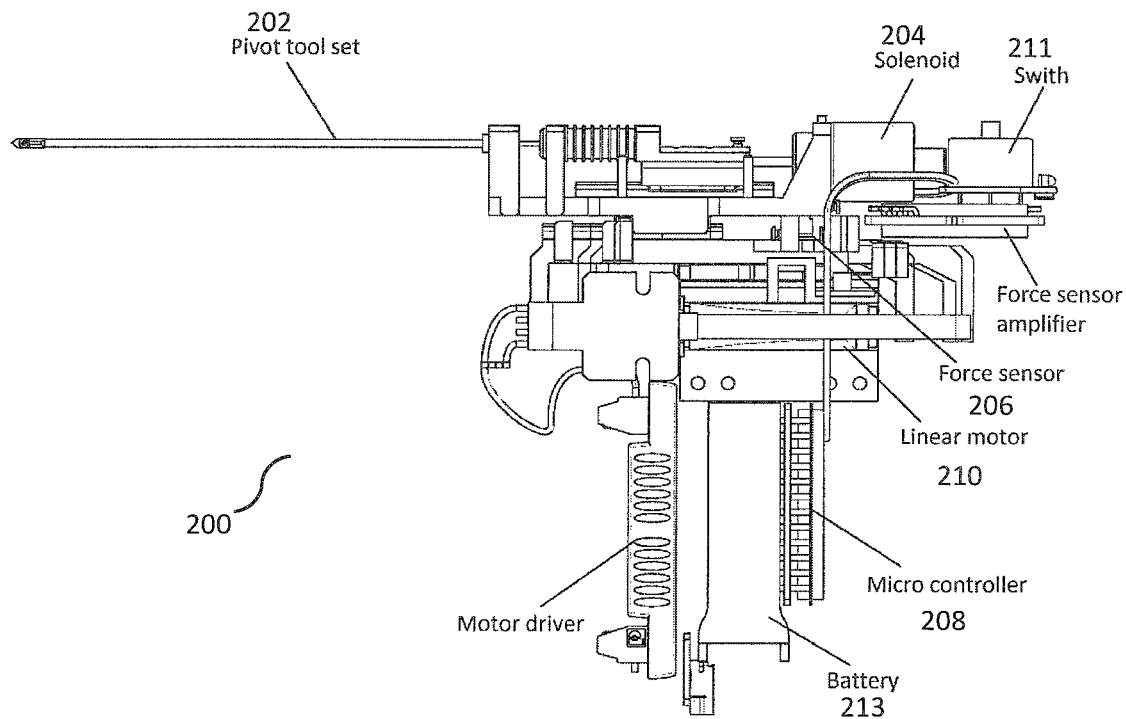
FIG. 2(a) shows a schematic drawing illustrating mechatronic setup according to an example embodiment, without housing.
Figures 2B, 2C:
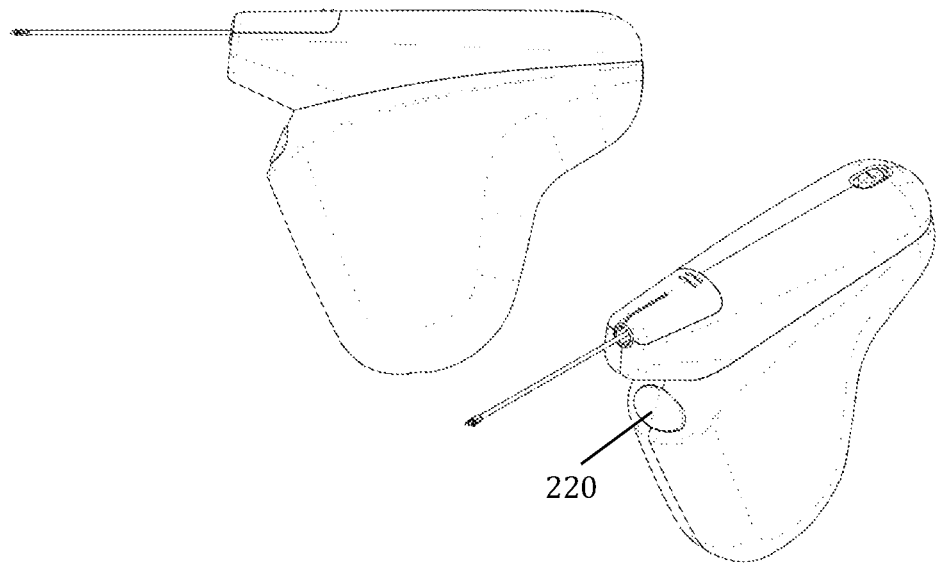
FIG. 2(b) shows a schematic drawing of the mechatronic setup of FIG. 2(a), with housing.
FIG. 2(c) shows a schematic drawing of a different view of the mechatronic setup of FIG. 2(b), with housing.

The design of the device according to example embodiments can include an ergonomic housing with the pivot tool set (which is a shaft assembly according to example embodiments). As shown in FIGS. 2(a), (b) and (c), a mechatronic setup design 200 according to an example embodiment consists of the mechanical structure including pivot tool set 202, the electrical actuators including solenoid 204 and linear motor 210, a switch button 211, a trigger button 220, the sensors including force sensor 206 and the micro controller 208, which can carry out the myringotomy with tube insertion automatically controlled by the micro controller 208. The force sensor 206 is used to sense and measure the contact force between the TM and the tip of the tool set 202, providing feedback to the microcontroller 208 which in turn synchronizes the mechanism of action of actuators controlling the tool set 202. The linear motor 210 is used for moving the tool set 202 and making the incision. The solenoid 204 is used for pushing the VT out for insertion. The user controls the device through the trigger button 220 with visual (such as light indicator) and audio (such as transducer) feedback provided by the mechatronic setup with integrated force sensing system, all powered by internal power supply (such as battery 213). The switch button 211 is a power switch, which is used to turn the device on and off. The switch button 211 can also be used to change between different modes (e.g., adult mode and child mode). The trigger button is used to activate the process of the device. Specifically, the procedure is as follow:

1) The surgeon turns on the power using the switch button 211.

2) The device is initialized by a program installed on the microcontroller 208.

3) The surgeon then locates the desired insertion location of the eardrum in the ear canal.

4) Once the surgeon is ready, the surgeon will press the trigger button 220 to activate the process.

5) Then the touch detection, myringotomy and grommet insertion will be processed by the device automatically, as will be described in more detail below.

Figure 2D:
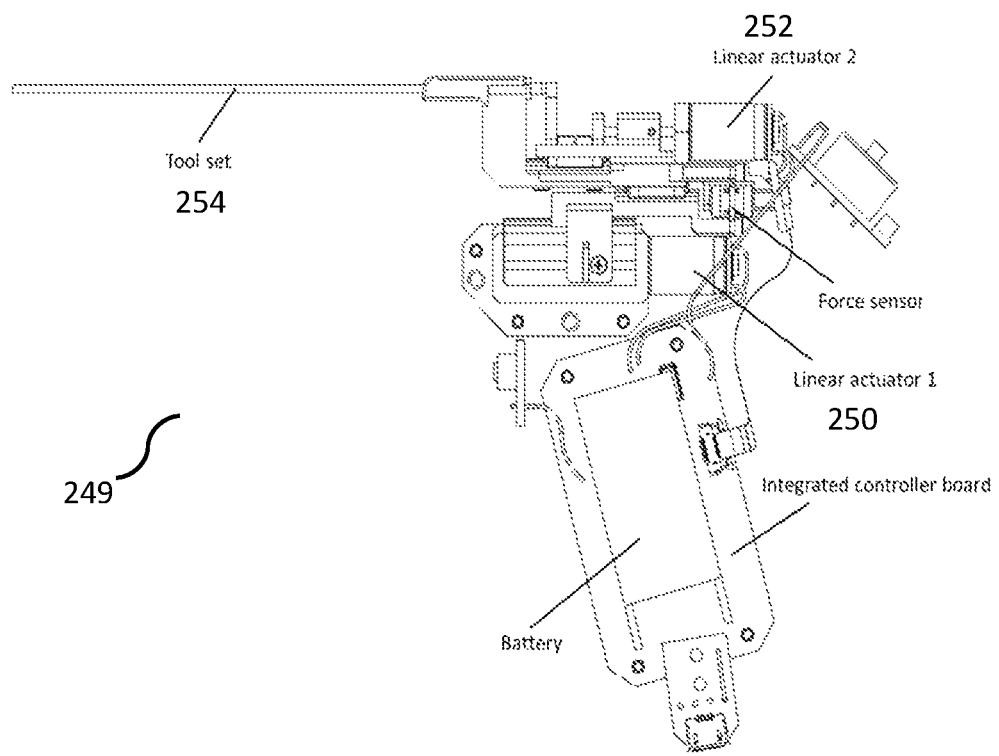
FIG. 2(d) shows a schematic drawing illustrating mechatronic setup according to another example embodiment, without housing.
Figures 2E, 2F:
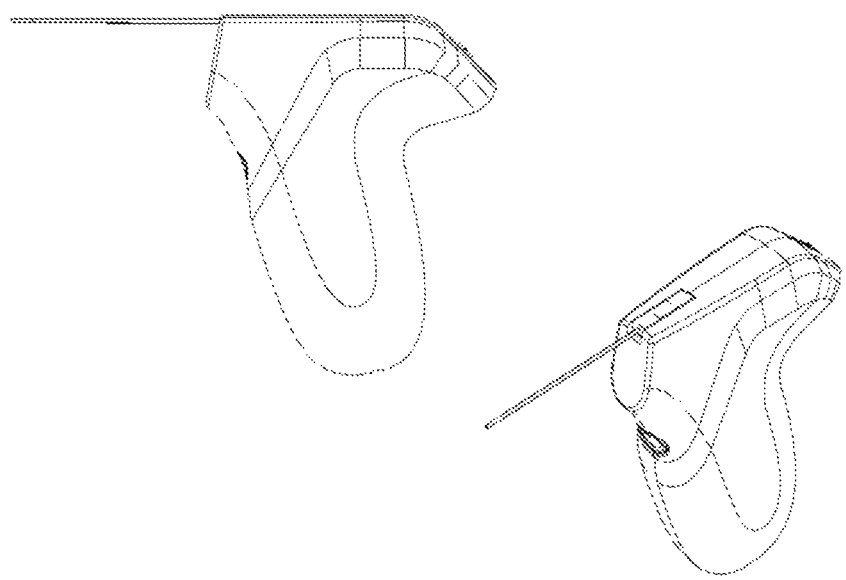
FIG. 2(e) shows a schematic drawing of the mechatronic setup of FIG. 2(d), with housing.
FIG. 2(f) shows a schematic drawing of a different view of the mechatronic setup of FIG. 2(e), with housing.

In the mechatronic setup design 249 according to another example embodiment shown in FIGS. 2(d), (e) and (f), the mechanical structure is slightly different in such a way that two same type of electrical linear actuators 250, 252 can be applied for moving the tool set 254, one making the incision and another pushing the VT out for insertion. The structural design and placement of components are alternatively arranged to maximize ergonomic of the device in this example embodiment, while the overall functioning and operation remains as described above with reference to the embodiments shown in FIGS. 2(a), (b) and (c).

In FIGS. 3(a) to (d), two mechanical setup designs according to example embodiments are shown, respectively, for assisting the surgeon to deploy the VT manually by pushing the button 300, 350. These two mechanical setup designs are based on the cam mechanism concept. Once the button 300 is pushed, the cam 302 of a rotary cam mechanism will rotate around the axle 304 and cause a linear movement of a cam follower 306 connected to one end of a pusher rod 308 disposed inside an outer tubing 308 coupled to the holder/cutter 310, and the pusher rod 308 in turn pushes out the VT (not shown). In the other example design, once the button 350 is pushed, the cam 352 of a linear cam mechanism will cause a linear movement of a cam follower 354 connected to one end of a guide wire coupled to a pusher rod disposed inside an outer tubing 356 coupled to the holder/cutter 358, and the pusher rod in turn pushes out the VT (not shown). The surgeon can control the pushing distance by controlling the pushing force on the button 300, 350.

Figure 3:
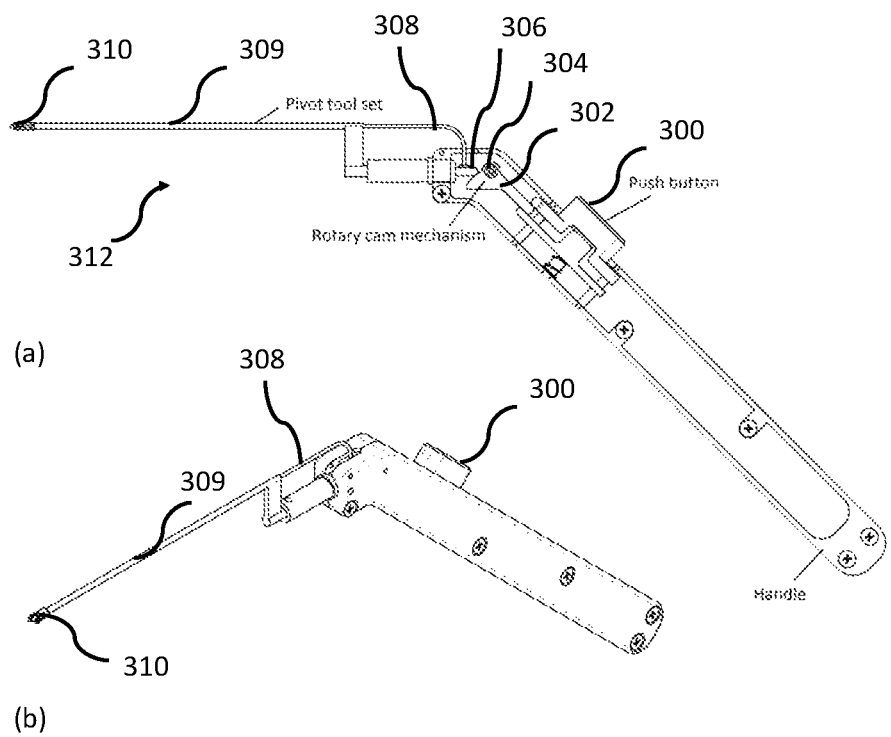
FIGS. 3(a) and (b) show a schematic side view, partially in cross-section, and a perspective view, respectively, of a mechanical setup design I, according to an example embodiment.
FIGS. 3(c) and (d) show a schematic side view, partially in cross-section, and a perspective view, respectively, of a mechanical setup design II, according to an example embodiment.
Figure 3:
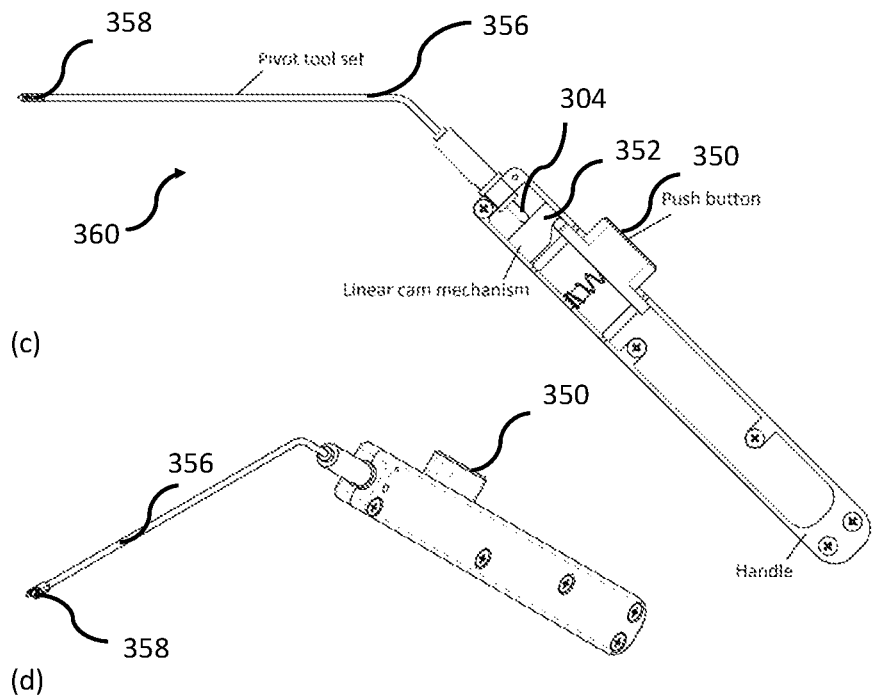
Figure 4:
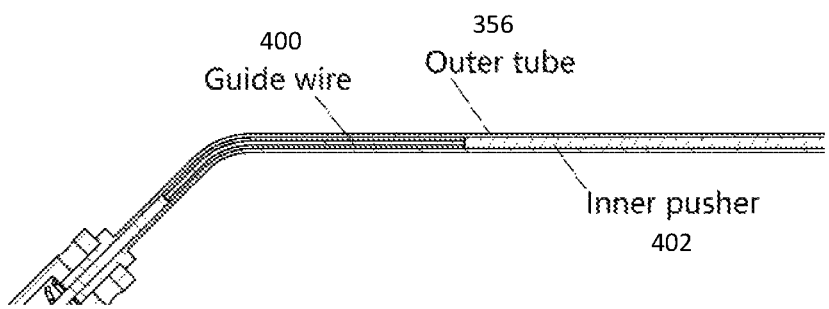
FIG. 4 shows a schematic cross-sectional view of a portion of the mechanical setup design II of FIGS. 3(c) and (d).
Figure 5:
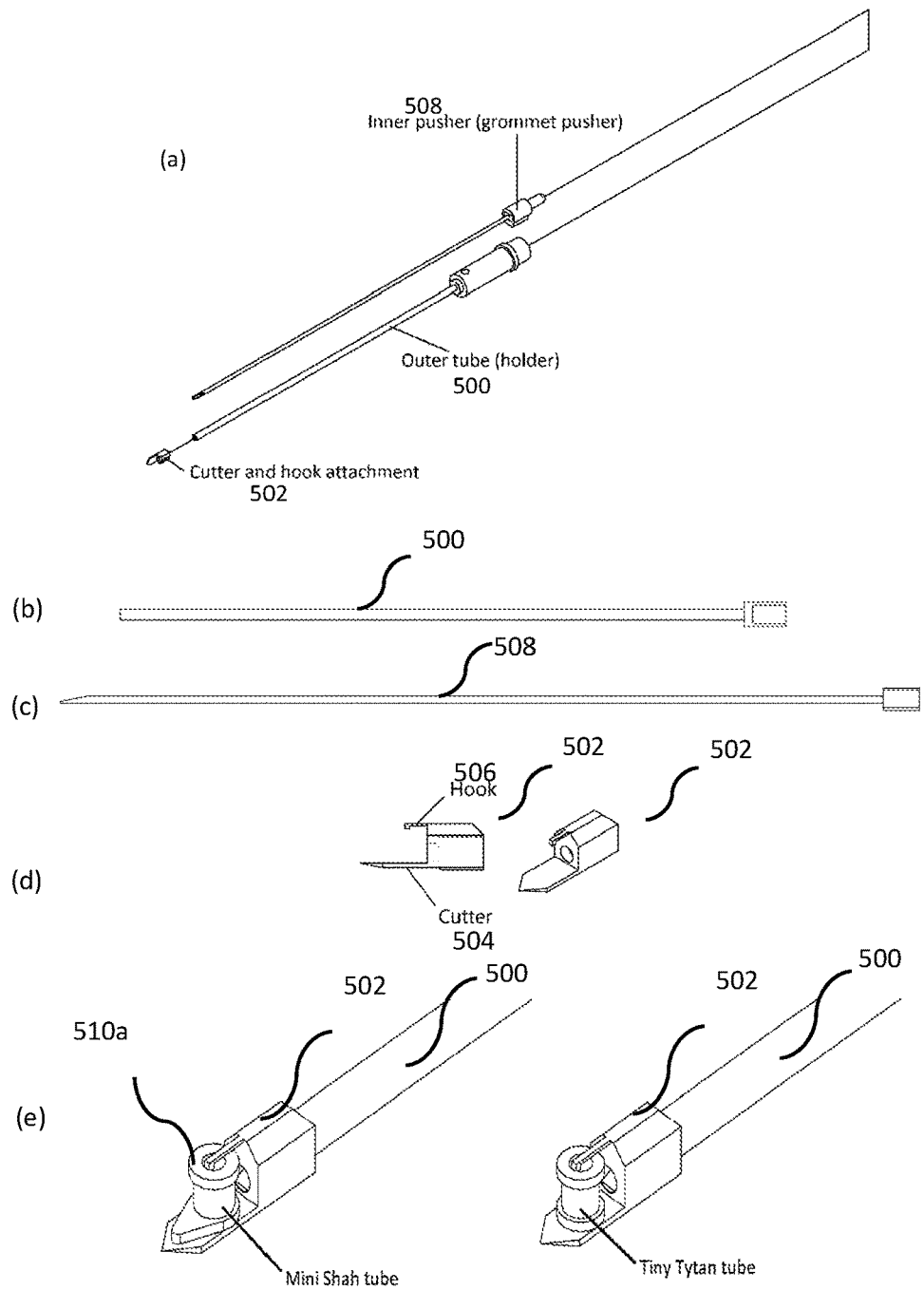
FIG. 5(a) shows a schematic exploded projection plot of a shaft assembly for a pivot tool set according to an example embodiment.
FIG. 5(b) shows a schematic drawing of the outer tube of the shaft assembly of FIG. 5(a).
FIG. 5(c) shows a schematic drawing of the inner pusher of the shaft assembly of FIG. 5(a).
FIG. 5(d) shows schematic side and perspective views of the cutter and hook attachment at the distal end of the outer tube of the shaft assembly of FIG. 5(a).
FIG. 5(e) shows schematic views of the cutter and hook attachment of FIG. 5(d) with different VTs loaded.

The pivot tool set for mechanical setup design I shown in FIG. 3(a) is a straight offset tool set 312 while the pivot tool set for mechanical setup design II shown in FIGS. 3(c) and (d) is a curve tool set 360 which is driven by the guide wire 400 disposed inside the outer tubing 356 and coupled to the inner pusher 402, as shown in FIG. 4.

Besides the cam mechanism design, the actuation system can be also changed to an electrical actuator such as voice coil motor or solenoid, etc. in different embodiments.

The shaft assembly of the pivot tool set according to example embodiments includes an outer tube 500, an attachment 502 with a cutter 504 at the bottom and a hook 506 at the top that is attached to the outer tube's 500 distal end, and an inner shaft 508 which is linearly moveable within the outer tube 500 acts as a pusher to push the VT 510a, b into the incision (see FIGS. 5(a)-(e). The VT 510 is loaded on the distal tip of the attachment 502 of the shaft assembly such that the VTs inner flange 512 is sitting on the cutter 504 and the device hook 506 clasps the VT's outer flange 514 at the top with the bent portion of the hook 506 inside the bore of the VT 510a, b (see FIG. 5(d)). The dimension of shaft assembly depends on the size of VT 510 such that the cutter 504 tip is extended from the loaded VT 510a, b and the height of the hook 506 is slight loosely fitted with the length of the VT 510a, b. An alternative arrangement can be for the hook 506 to be made of a flexible and bendable material that allows VTs of slightly variable height to be used, according to other example embodiments.

VT tubes are generally classified into two major categories; pediatric- and adult-sized VT. Tiny Tytan and Shah Type VT are pediatric-sized VT that shares the same lumen (inner) as well as outer diameter, which are 0.76 mm and 1.5-1.6 mm, respectively. They also have the same tube body length of 1.5-1.6 mm. On the other hand, there are more variety of adult-sized VT design. However, the lumen (inner) diameter of most commonly used adult-sized VT usually ranges only from 1.14-1.27 mm, with tube body length ranges from 2.3-2.8 mm.

Figure 6:
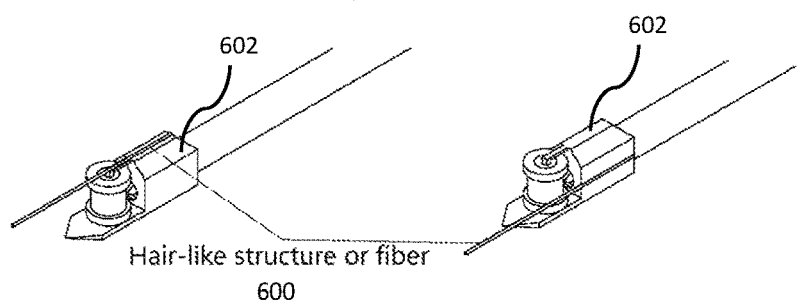
FIG. 6 shows perspective views of shaft assemblies with hair-like structure or fiber, according to example embodiments.

The pivot tool set 304, 354 is attached to an actuation system which can be a fully mechanical setup according to example embodiments, comprising of a spring system (see FIGS. 3(*a*) and (*b*)) or the pivot tool set 202 can contain electrical components including force sensors 206 and actuators 204, 210 to allow automatic detection when the cutter touches the TM, and automatic actuation after the touch (see FIGS. 2(*a*) and (*b*)). In both setups, a hair-like structure or fiber (e.g., suture) 600 can be attached to the tip of the attachment 602 as shown in FIG. 6. The hair-like structure 600 can provide a method of proximity sensing when bringing the device closer to the eardrum before commencing the surgical procedure. Upon touching the eardrum, the deflection or displacement of the structure 600 serves as a signal to inform the surgeon that the applicator is sufficiently close to the eardrum to begin with the surgical procedure. This method could potentially minimize the contact time and the amount of force to be exerted on the eardrum compared to that without using any such structure, according to example embodiments. This method of proximity sensing according to example embodiments is explained further below.

Figure 7:
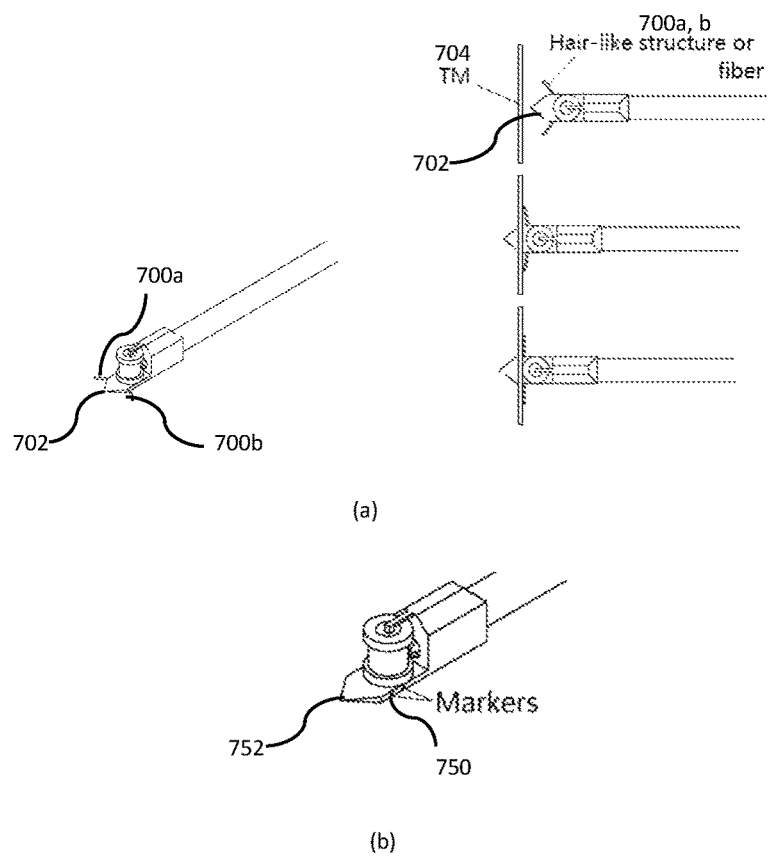
FIG. 7(a) shows a schematic perspective view and a sequence of schematic top views illustrating using hair-like structure or fiber mechanism for incision depth detection, according to example embodiments.
FIG. 7(b) shows a schematic perspective view of a cutter with marker(s) for incision depth detection, according to an example embodiment.

Similarly, when a curve hair-like structure or fiber 700*a*, 700*b* is placed under the cutter 702 with a fixed distance as shown in FIG. 7(*a*) according to example embodiments, it can be used for detecting the incision depth (the distance from the cutter 702 tip incised on the TM 704 to the surface of the TM). As can be seen in FIG. 7(*a*), the structure 700*a*, 700*b* (e.g., suture) will become straighter while the cutter 702 incises deeper into the TM 704. Alternatively, as shown in FIG. 7(*b*), a marker e.g. 750 on the cutter 752 showing a fixed distance (e.g., 2.5 mm) from the cutter 752 tip to the marker 750 can be also used for the incision depth detection. In other words, when the surgeon sees that the TM is on the marker 750, he/she will notice how deep the cutter 752 goes into the TM. Different colours of the markers e.g. 750 can be used to indicate different distances in an example embodiment, and different widths of the markers can be used to set different tolerances in an example embodiment.

In the following, the procedural steps while the device according to example embodiments is employed are described:

Step 1. Surgeon visualizes the patient's ear drum and notes the best VT insertion site.

Step 2. Surgeon prepares the device by fixing the tool set in the correct direction/orientation onto the device. The VT can come preloaded on the tool set or be loaded onto the tool set/device in an upright position by the surgeon.

Step 3. A normal speculum can be inserted into the outer ear canal. Under visualization by microscope or surgical loupes, the tool set is manually advanced into the ear canal until the tip of the hair-like structure touches the eardrum, which is indicated by a deflection of the structure. The tool set will then be around 3-4 mm away from the designated insertion site, according to example embodiments.

Step 4 (automatic operation according to an example embodiment).

Figure 8:
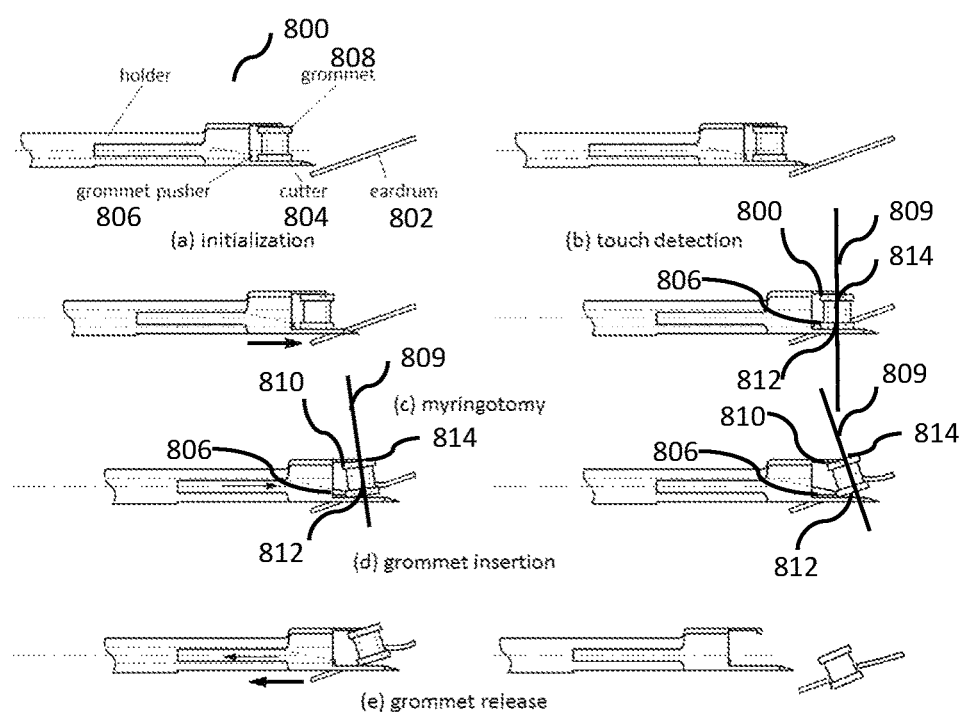
FIGS. 8(a)-(e) show partial cross-sectional views of a pivot tool set for automatic insertion using a mechanical and electrical device, according to an example embodiment.
Figure 16:
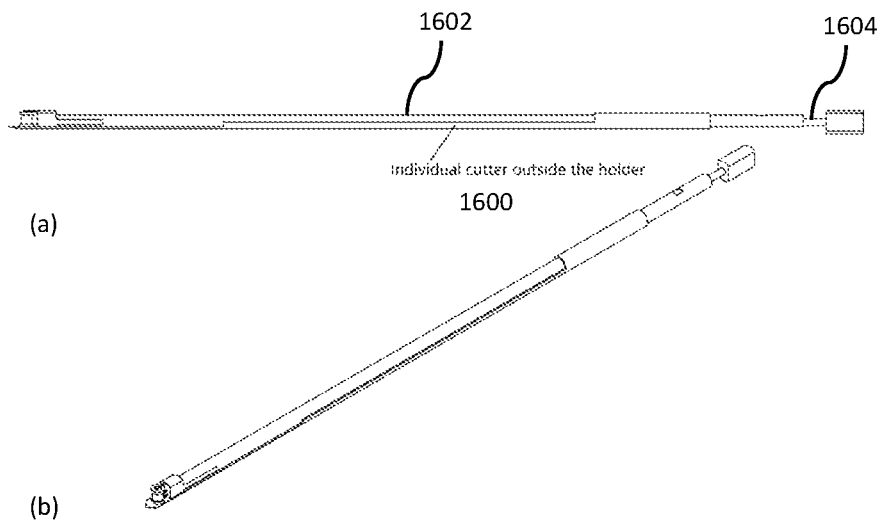
FIG. 16 shows schematic side and perspective views of a pivot tool set with a movable outer cutter, according to an example embodiment.
Figure 17:
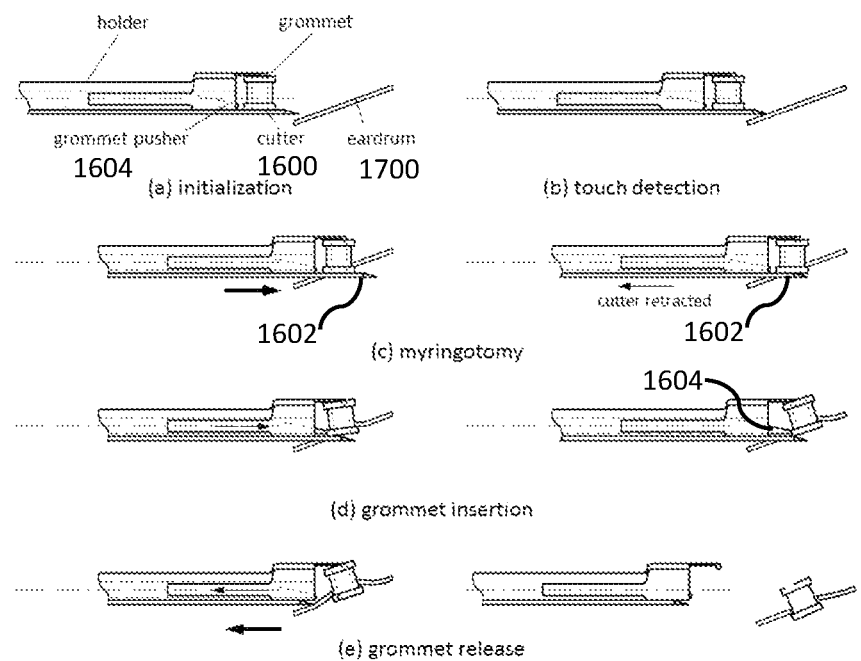
FIG. 17(a)-(e) show partial cross-sectional schematic views of the pivot tool set of FIG. 15 illustrating a working process of the movable cutter.

For automatic operation, after initialization (step 3, compare FIG. 8(*a*)), a foot pedal or a switch is activated according to an example embodiment. The motor in the device will then move the tool set 800 forward slowly until the force sensor registers that the tool set 800 has touched the eardrum 802, as illustrated in FIG. 8(*b*). The motor then moves the tool set 800 forward such that the cutter element, here in the form of cutter 804, pierces the eardrum 802 in the designated insertion site, as illustrated in FIG. 8(*c*). The pusher 806 then moves forward to push the lower end of the VT, here a grommet 808, into the incision, as illustrated in FIG. 8(*d*). Together with the hook 810 at the top, this creates a torque that rotates the grommet 808 into the incision, as illustrated in FIG. 8(*d*). In other words, a holder member of the device, here in the form of the upper surface of the cutter 804, is configured to dispose the grommet 808 in an orientation in which a longitudinal axis 809 of the grommet 808 is substantially perpendicular to the cutter 804, and a pusher member of the device, here in the form pusher 806, is configured to apply a pushing force to a first end 812 of the grommet 808 in a direction substantially perpendicular to the longitudinal axis 809, the first end 812 of the grommet 808 being disposed closer to the cutter 804 than a second end 814 of the grommet 808. Substantially perpendicular to the longitudinal axis 809 is intended to cover the various orientations between the pushing force applied by the pusher 806 and the longitudinal axis 809 during the pivoting for insertion of the grommet 808, noting that for each orientation, there is at least a component of the pushing force that is exactly perpendicular to the longitudinal axis 809, as will be appreciated by a person skilled in the art. A pivot member of the device, here in the form of hook 810, is configured to releasably engage the second end 814 of the grommet 808 such that the grommet 808 is pivotable about the hook 810 under the pushing force applied to the first end 812 of the grommet 808 by the pusher 806, for insertion of the first end 812 of the grommet T 808 into the incision. As shown in FIG. 8(*e*), the rim of the grommet 808 being "anchored" in the incision can preferably resist the pullout from the incision to a good extent because the withdrawal time of the tool set (pusher 806 and cutter 804) is generally quick with low friction between the cutter 804 and the grommet 808. The withdrawal speed (or time) is preferably optimized to achieve this. Furthermore, the resistance against pulling out the grommet 808 during tool set withdrawal can be strengthened in different embodiments which will be described in more detail with reference to FIGS. 16 and 17 below, where the cutter is withdrawn first while the VT is fully anchored by the ear membrane before withdrawing the tool set with the hook. The average time of operation of automatic insertion is less than two seconds, according to example embodiments.

Step 4 (manual operation according to an example embodiment).

Figure 9:
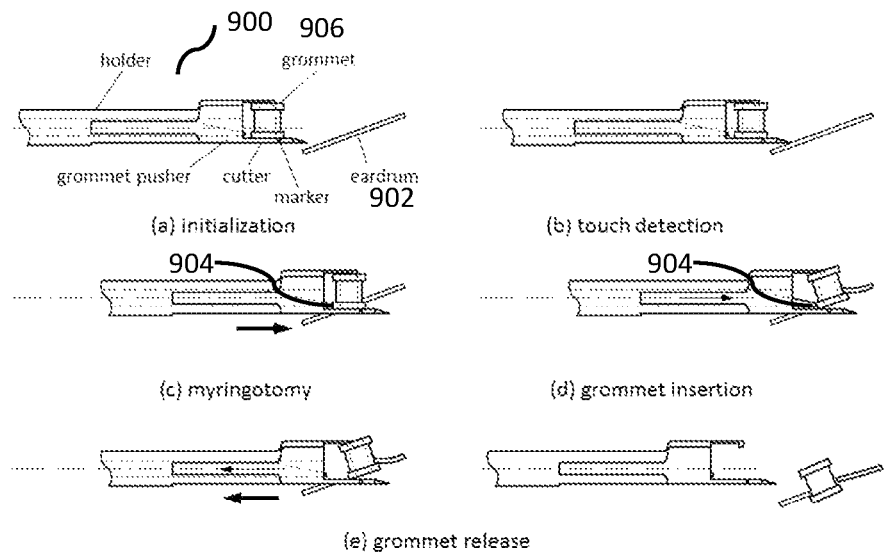
FIGS. 9(a)-(e) show partial cross-sectional schematic views of a pivot tool set for manual insertion using a fully mechanical device, according to an example embodiment.
Figure 10:
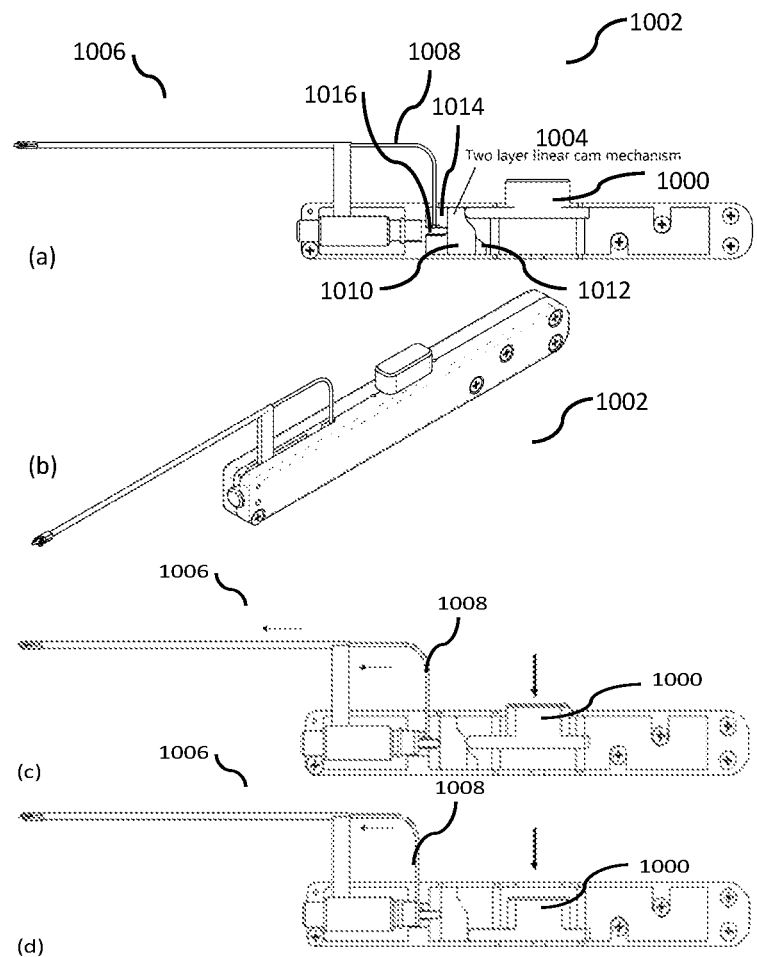
FIGS. 10(a) and (b) show a schematic side view, partially in cross-section, and a perspective view, respectively, of a semiauto mechanical setup design, according to an example embodiment.
FIGS. 10(c) and (d) show schematic side views, partially in cross-section, illustrating operation of the semiauto mechanical setup design, according to an example embodiment.

For manual operation, after initialization (step 3, compare FIG. 9(*a*)), the surgeon brings the device/tool set 900 towards the TM, here eardrum 902. Once the device/tool set 900 touches the eardrum 902, the surgeon can sense the touching force to his/her hand as illustrated in FIG. 9(*b*), and then the surgeon can directly push the device/tool set 900 forward to incise the eardrum 902 until he/she feels an obvious force changing or is indicated by the methods descripted above with reference to FIG. 7(*a*) or (*b*), as illustrated in FIG. 9(*c*). Following that, the surgeon can activate the inner pusher 904 to tilt or pivot the VT, here in the form of a grommet 906, into the incision, as illustrated in FIG. 9(*d*). Finally, the surgeon withdraws the device/tool set after the grommet 906 has been inserted, as illustrated in FIG. 9(*e*).

Step 4 (semi-automatic operation according to an example embodiment).

The semi-auto operation is realized by another fully mechanical setup design of a device 1001 according to an example embodiment (see FIGS. 10(a) to (d)) that is modified based on the mechanical setup design I embodiment shown in FIG. 3(a). For semi-auto operation, the surgeon manually brings the tip of the tool set to touch the TM. Next, the surgeon presses the button 1000 on the device 1002 and the device 1002 will make an incision on the TM and then insert the VT into the incision automatically in sequence. That is, the operation is actuated by a mechanical system instead of the operation being actuated by the mechatronic system as described above with reference to FIG. 8. In the cam mechanism 1004, there are two separate linear cams 1010, 1012 with separate cam followers 1014, 1016, one for movement the whole pivot tool set 1006 (see FIG. 10(c)) and the other for movement of the inner pusher 1008 (see FIG. 10(d)), to allow for two separate movements of the whole pivot tool set 1006 and the inner pusher 1008 individually, according to an example embodiment.

Experimental Results

Figure 11:
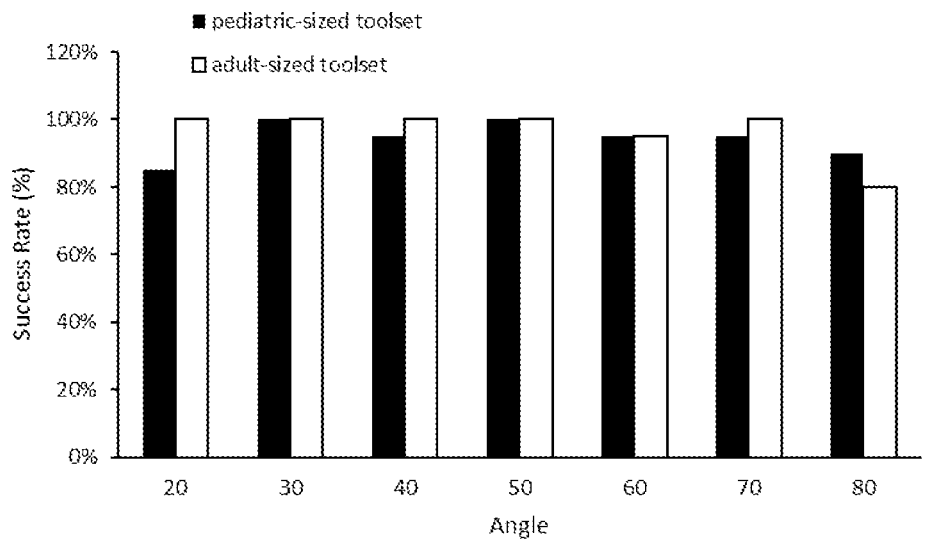
FIG. 11(a) shows a chart illustrating experimental results, specifically first-attempt success rate on mock membranes for a paediatric-sized and adult-sized tool sets according to example embodiments.
FIG. 11(b) shows a chart illustrating experimental results, specifically average insertion force on mock membranes for a paediatric-sized and adult-sized tool sets according to example embodiments.
Figure 11:
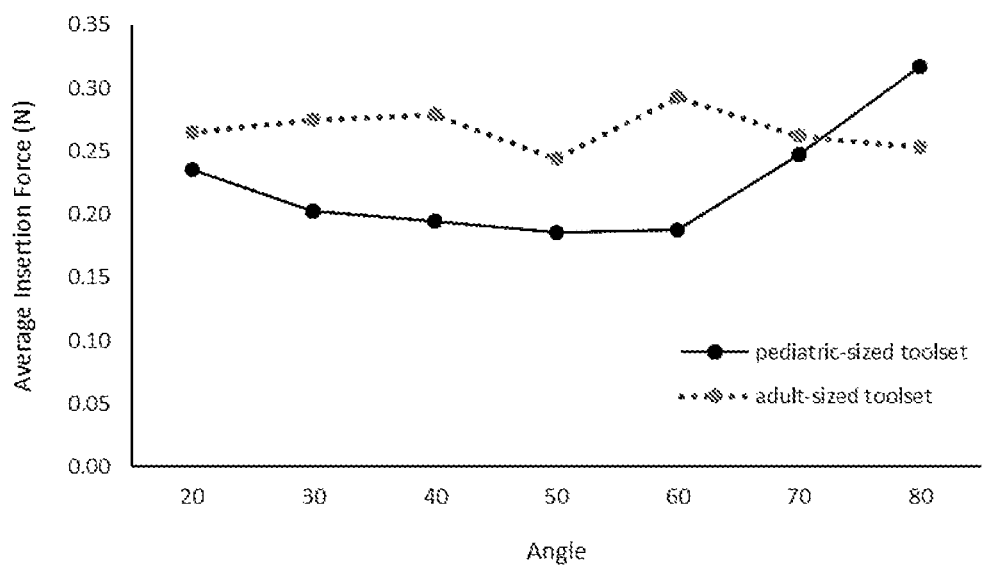

A force sensing stage with a mock membrane holder was used to simulate a mock TM and to measure the force applied on it. In this experiment, polyvinyl chloride (or commonly known as cling wrap) was chosen as mock TM material. Polyvinyl chloride's elastic modulus falls within previously published range of TM's, thus most realistic in regards to the stabbing force during VTA's myringotomy procedure, and is convenient and widely available. The mock membrane holder is sloped at different degrees ranging from 20 degrees to 80 degrees to mimic the obliqueness of the eardrum. A mechatronic setup with fully automatic operation according to an example embodiment (compare FIGS. 2(a) and (b) described above) was used for this experiment. A Tiny Tytan ventilation tube was used for the paediatric-sized tool set and Shah Activent tube was used for the adult-sized tool set. 20 trials were conducted per angle, hence a total of 140 trials were conducted for each tool set type. The number of first attempt successful insertions as well as the insertion force were recorded and shown in the charts in FIGS. 11(a) and (b), respectively.

As shown in tables 1 and 2, example embodiments advantageously provided high success rate and low insertion force. Additionally, while for extremely oblique angles such as those below 20°, the first-attempt success rate of tube deployment decreases in these experiments, such cases can further be addressed using various modified embodiments, e.g. using cutter and pusher such as those illustrated in FIG. 18(a) or FIG. 18(e), described below.

Incorporation of Hair-Like Structure or Fiber as Proximity Sensing, According to Example Embodiments The inclusion of a hair-like structure on the tool set according to example embodiments is deemed to facilitate office-based ventilation tube insertion procedure in a few aspects as follows:
  It allows surgeon to confidently maintain a desired distance of the tip of the device from human eardrum before activating the device for myringotomy and grommet insertion.
  A simple method to guide and pinpoint the desired spot on eardrum without the need to seek the desired spot by pressing the device's tip on the eardrum for an appreciable amount of time. Longer contact time of device's tip with the eardrum would create discomfort or pain to patients. On the contrary, the touch on eardrum by a fine strand of hair-like structure could minimize the contact time and thus discomfort level. The finer the structure strand, the lesser touch sensation on the eardrum according to example embodiments.
  The hair-like structure can be conveniently included in the device tool set without complicating the assembling or manufacturing process of the device according to example embodiments. The structure includes, but is not limited to, biodegradable suture. The advantage of using biodegradable suture is that it is commercially available in many sizes, biocompatible and comes in sterile condition and readily used. The bio-absorbable nature of the suture according to preferred embodiments is to ensure there will not be any unnecessary reaction if the suture is by chance left in the ear during the procedure. The suture can drop out of or self-resorb in the ear without any unwanted adverse event.

The strand of suture can be included by at least two methods, by way of example, not limitation, (1) with the suture firmly fixed on the tool set, or (2) the suture loosely adhering to the tool set by use of a lubricant.

Method 1

In this method, a strand of suture is placed and fixed stably on the tool set. The method of fixing can be done by using sterile tape such as biocompatible Steri-Strip™ by 3M or other biocompatible glues. The suture is fixed in such a way that a short segment is protruded out of the tool set at a preferred distance (3 mm or less). When the system approaches the eardrum, the suture is deflected. The deflection can be seen under microscope or surgical eye loupe and serves as a proximity feedback to surgeon that the applicator device is within a zone that it can be activated for myringotomy and grommet tube insertion.

Method 2

This method requires a strand of suture to be loosely adhering to the surface of the tool set by applying a small drop of lubricant to the suture. Although the suture is not fixed to the tool set, it is held in place by the surface tension of the lubricant, yet allows the suture to move slightly when it touches the eardrum. Similar to Method 1, a short segment of the suture is protruded out of the tool set at a preferred distance (3 mm or less). The protruded segment of suture can be visualized by surgeon under the microscope or a surgical eye loupe. When surgeon brings the suture to the eardrum, the suture is either slightly deflected or displaced or both upon touch.

Figure 12:
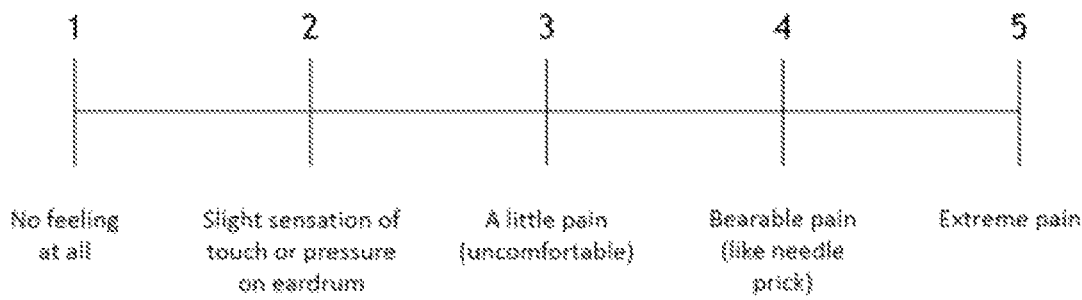
FIG. 12 shows a pain rating chart from scale of 1 to 5, used to obtain volunteer feedback for applying a tool set with a hair-like structure or fiber mechanism according to example embodiments.

The methods 1 and 2 of suture inclusion according to example embodiments described above have been verified by an ENT surgeon on two volunteers, and have been shown to work well as a proximity sensing tool on the device during cadaver tests. Generally, the suture that is protruded out from the tool set provides surgeon with sufficient visualization of the suture when the tool set is brought towards the eardrum. Dyed suture with darker colours are easier to be noticed under microscope than undyed suture when the set-up are placed in the ear canal. During the testing on volunteers where the surgeon touched healthy eardrum with the suture, both volunteers were asked to rate the sensation from 1 to 5, with 1 being no feeling at all and 5 being extreme pain (see FIG. 12). No analgesic was ingested nor local anesthesia applied to the eardrum. When the suture is fixed onto the tool set with a sterile tape, the average rating is 2.4. For the free-moving suture, the average rating is 1.3. From the results, it can be seen that a fixed suture caused slightly more discomfort than a free-moving one upon gentle touch of the suture on the eardrum. This is likely due to a greater force exerted by suture that is fixed on the tool set. However, as both methods did not cause any significant pain to the eardrums without any analgesic or local anesthesia, the methods were verified to be a simple and feasible way to obtain a reasonable resolution of proximity sensing for surgeon, according to example embodiments.

Different Designs of Pivot Tool Set, According to Example Embodiments

The design of the pivot tool set is not limited to the design as described above with reference to FIG. 5, but can be designed differently according to different embodiments so as to provide a device capable of facilitating the movements involved in the method according to example embodiments. Some alternative designs will now be described, by way of example, not limitation.

1) Inner Pusher in Different Shapes According to Example Embodiments

Figure 13:
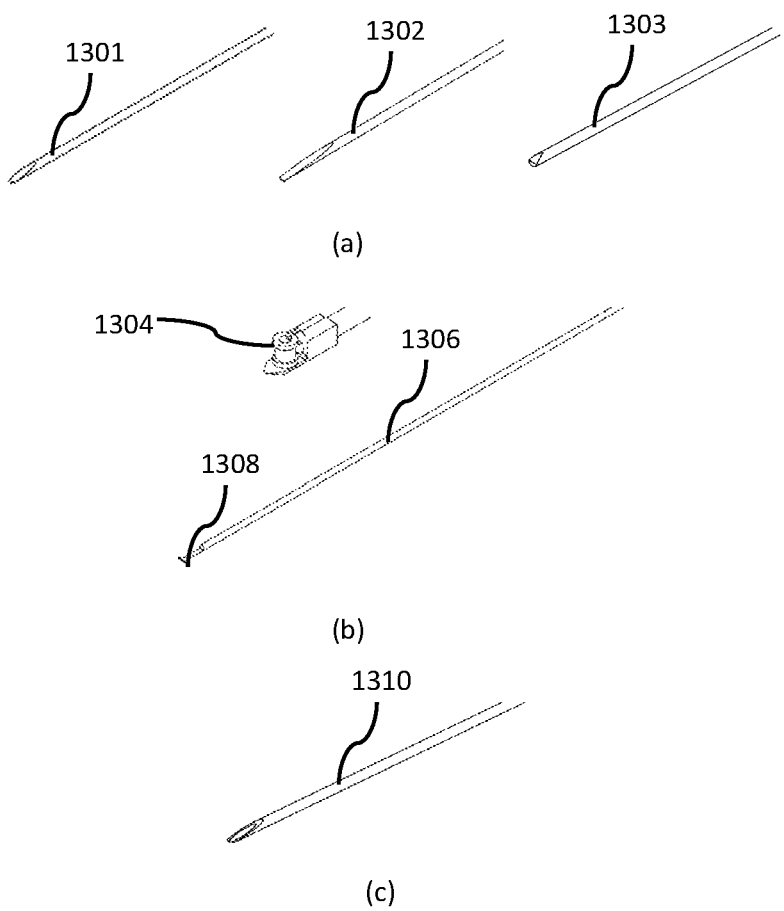
FIG. 13(a) shows a schematic perspective view of a solid inner pushers with different curvatures, according to an example embodiments.
FIG. 13(b) shows a schematic perspective view of an inner pusher with wide head, according to an example embodiment.
FIG. 13(c) shows a schematic perspective view of an inner hollow pusher, according to an example embodiment.

FIGS. 13(a) to (c) show different designs of the inner pusher according to example embodiments. The main function of the inner pusher is to apply a forward force on the inner flange of the VT (i.e. the first end of the VT that is closer to the blade). There can be several designs of the inner pusher that can achieve this aim, as long as the pusher preferably exerts a force only on one side of the VT, for example, a pusher that has a sloping end and the slope can be of different gradient and curvatures, as shown for different pushers 1301-1303 in FIG. 13(a). The different designs of inner pusher can also give different pivoting angle/effect of the VT as required, depending for example on the angle of TM that the VT needs to negotiate. Furthermore, for a VT 1304 with a wider inner flange a pusher 1306 with a wider head 1308 can be used, as shown in FIG. 13(b). The pusher 1310 can also be a hollow member to reduce the weight of the toolset, as shown in FIG. 13(c).

2) Pusher at the Outer Core According to Example Embodiments

Figure 14:
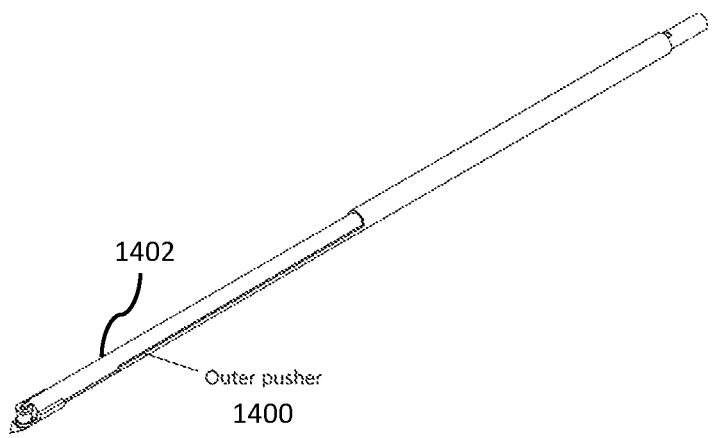
FIG. 14 shows a schematic perspective view of a pivot tool set with a pusher configured at the outer core, according to an example embodiment.
Figure 15:
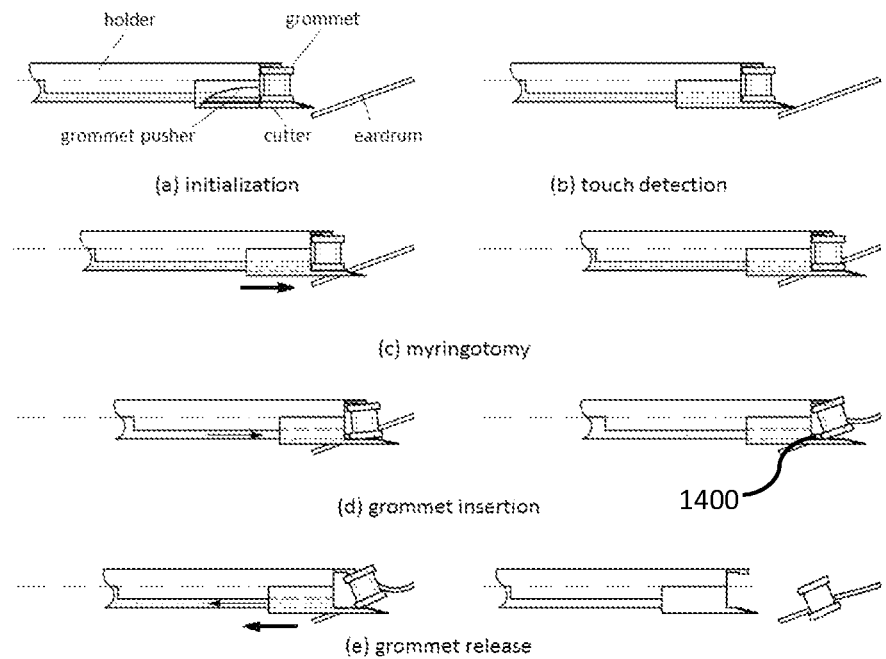
FIG. 15(a)-(e) show partial cross-sectional views of the pivot tool set of FIG. 13 illustrating a working process of the outer pusher.

The VT pusher 1400 can be placed at the outer core (i.e. cover the outer tube 1402), as shown in FIG. 14. FIGS. 15(a)-(e) show the working process of this design according to an example embodiment. With this design, the pusher 1400 can be wider and in different shape so that the tool set can fit different types of VTs or grommets, according to example embodiments.

3) Movable Outer Cutter Design According to Example Embodiments

Figure 18:
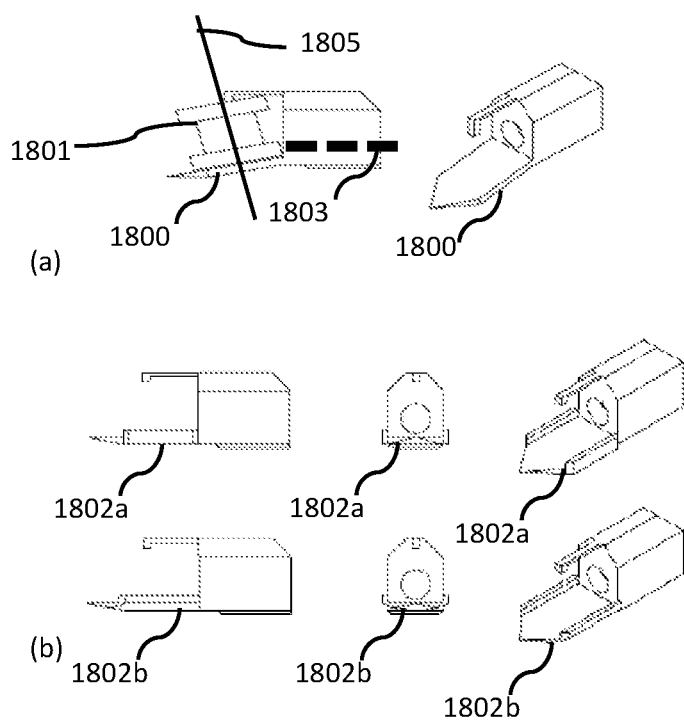
FIG. 18(a) shows schematic side and perspective views of a tilted cutter according to an example embodiment.
FIG. 18(b) shows schematic side, front and perspective views of two crescentic cutters according to example embodiments.
FIG. 18(c) shows schematic top and perspective views of a two-step/multi-step cutter according to an example embodiment.
FIG. 18(d) shows schematic side, top and perspective views of a bevel cutter according to an example embodiment.
FIG. 18(e) shows schematic side, top and perspective views of horizontal cutters according to example embodiments.
FIG. 18(f) shows schematic drawings illustrating grommet insertion operation by a horizontal cutter according to example embodiment.
Figure 18:
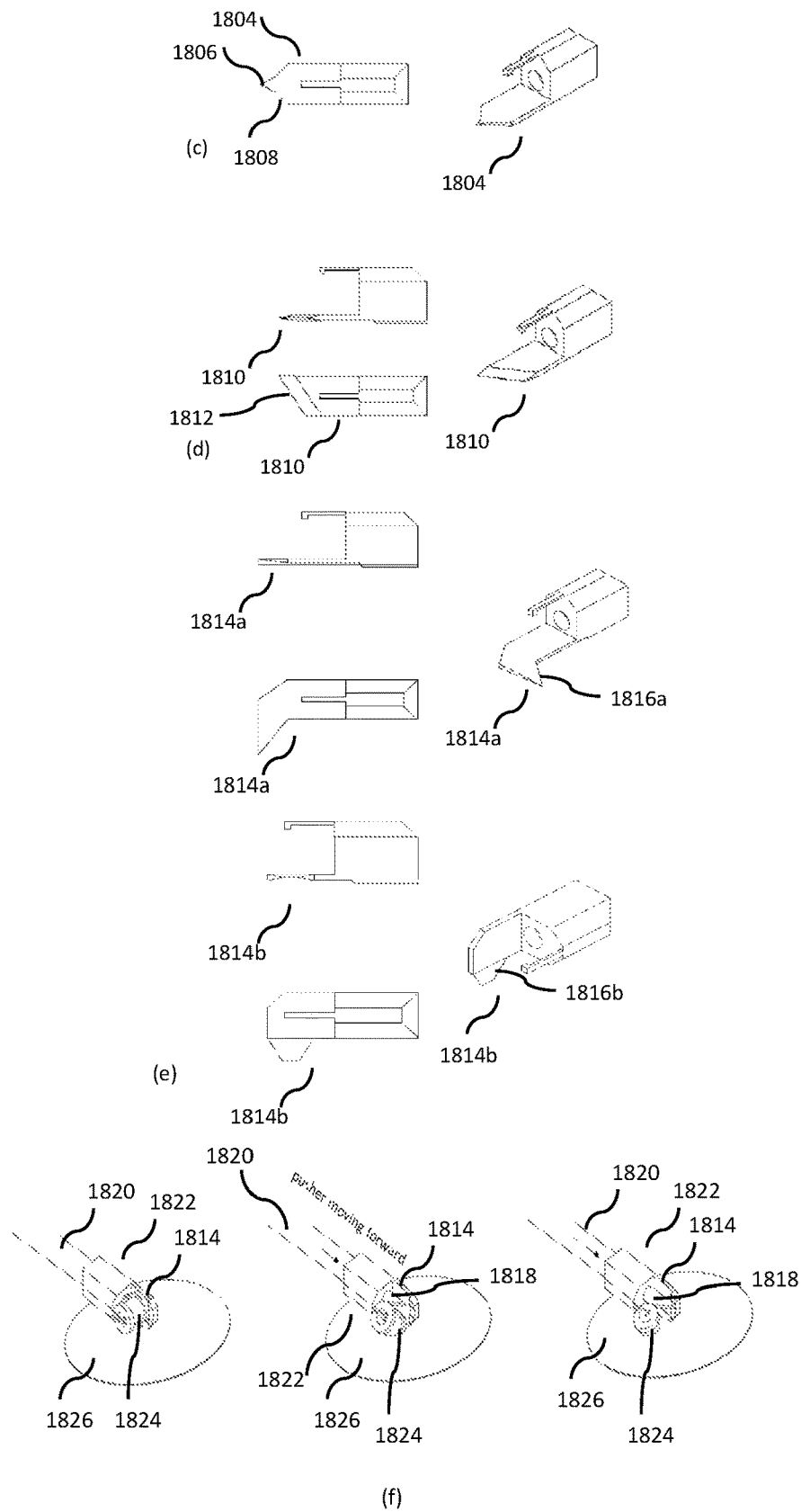

Instead of the fixed cutter on the tip, a movable cutter 1600 can be also designed to be placed outside the outer tube 1602 with an inner pusher 1604, as shown in the tool set of FIGS. 16(a) and (b). The working process is shown in FIGS. 18(1)-(2). The movable cutter 1600 can be driven individually or correlated with the inner pusher 1604. The cutter 1600 can be retracted before the punch out of the inner pusher 1604 to insert the VT into the TM, here the eardrum 1700, in such embodiments, as illustrated in FIGS. 17(c) and (d).

4) Cutter in Different Shapes and Attached at Different Angles, According to Example Embodiments FIGS. 18(a)-(e) show different designs of cutters, which can be used in different user cases. For example, the tilted cutter 1800 can be used in the case that the eardrum angle is extremely close to horizontal (less than 20 deg). As shown in FIG. 18(a), the VT 1801 would remain perpendicular to the tilted cutter 1800 in order to negotiate the extremely horizontal TM angle. The perpendicular position of the VT 1801 with respect to the tilted cutter 1800 is preferred so that the flange of the VT 1801 adjacent to the tilted cutter would be guided smoothly into the slit on the TM once the incision is made by the tilted cutter 1800. Again, it is noted that there is at least a component of the pushing force applied to the VT 1801 by the pusher 1803 in such embodiments that is exactly perpendicular to the longitudinal axis 1805, as will be appreciated by a person skilled in the art.

The crescentic cutter 1802a,b can be used in the case that the eardrum is thick, which can also help to make the incision larger and prevent the VT from dropping. The crescentic cutter 1802a with higher crescent on each side could be used with some VT types that have a slightly thicker flange that sits on the cutter 1802a to ease the VT insertion whilst the crescentic cutter 1802b with lower crescent could be used for VT with thinner flange. The two-step/multi-step cutter 1804 with a steeper tip 1806 followed by one or more sections 1808 of slighter incline can help to reduce the incision force while the incision can be kept the same. The bevel cutter 1810 (i.e. blade 1812 at the side) can behave like a surgical knife, which can potentially reduce the force. The horizontal cutters 1814a, b have an off-axis blade 1816a, b, as shown in FIG. 18(d). The working process of the horizontal cutter 1814 during VT insertion is shown in the FIG. 18(f). By pushing out the pusher 1818 inside the outer tube 1820 (and attachment/holder 1822), the VT 1824 will be pivoted and rotated by the sloped and suitably oriented end 1826 of the pusher 1818 towards the membrane 1826 with very low angle, for insertion into the incision made by the blade.

Figure 19:
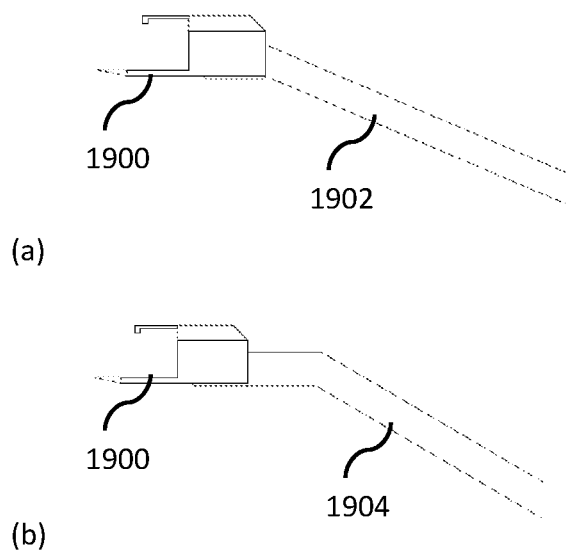
FIG. 19(a) shows a schematic side view of a cutter attached to a shaft at a different angle, according to an example embodiment.
FIG. 19(b) shows a schematic side view of a cutter attached to a shaft with a curved tip, according to an example embodiment.

The cutter 1900 can also be attached to the shaft 1902 at different angles so as to accommodate TM angles from 0-20 degree, as shown in FIG. 19(a). The shaft 1904 can also be slightly bent or curved to achieve the same effect, as shown In FIG. 19(b). In such embodiments, guide wire can be used to obtain "curved" pusher movement.

5) Hook in Different Shapes, According to Example Embodiments

Figure 20:
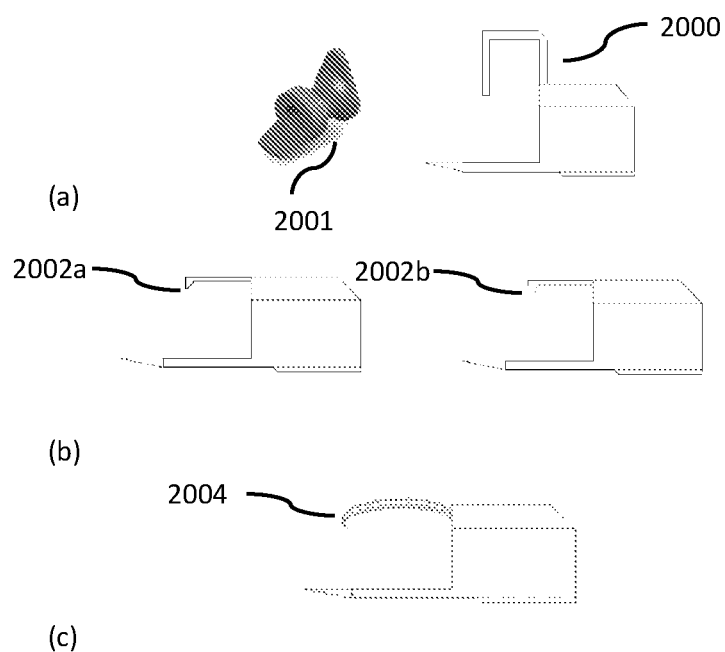
FIG. 20(a) shows a schematic side view of a hook design for a VT with a tab, according to an example embodiment.
FIG. 20(b) shows a schematic side view of a chamfered hook design, according to an example embodiment.
FIG. 20(c) shows a schematic side view of a brush hook design, according to an example embodiment.

FIGS. 20(a) to (c) show the hook in different forms and shapes to fit different types of VTs according to example embodiments, e.g. FIG. 20(a) shows a hook design 2000 specially designed for VT 2001 with a tab. The hook 2002 can also be a chamfered design (see FIG. 20(b)). The chamfered design of the hook 2002a, b may be suitable if the VT does not require much engagement for pivoting, and the reduced contact with the inner bore of the VT can assist in the subsequent release of the VT after the pivot. FIG. 20(c) shows the hook 2004 with a bristly or brush-type design with curved thins strands. The flexible strands would be able to achieve the same effect as the hook design and can be used for VT that may not have a regular shape or if the inner bore of the VT is not directly in line with the central axis. The flexible strands hook 2004 design is able to fit VT of different heights so that a tool set change is preferably not required if different type of VT is used, e.g. for the left or right ear TM.

Figure 21:
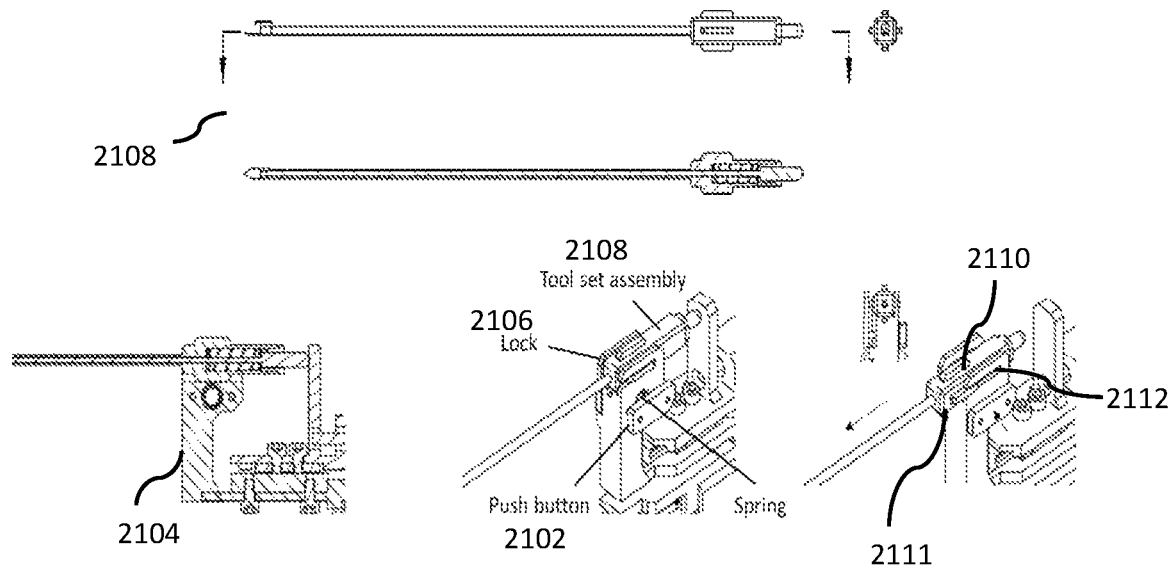
In FIG. 21(a) shows schematic drawings illustrating different views of an interface for a push-and-lock mechanism of a tool set, according to an example embodiment.
In FIG. 21(b) shows schematic drawings illustrating different views of an interface for a quick-lock mechanism of a tool set according to an example embodiment.
Figure 21:
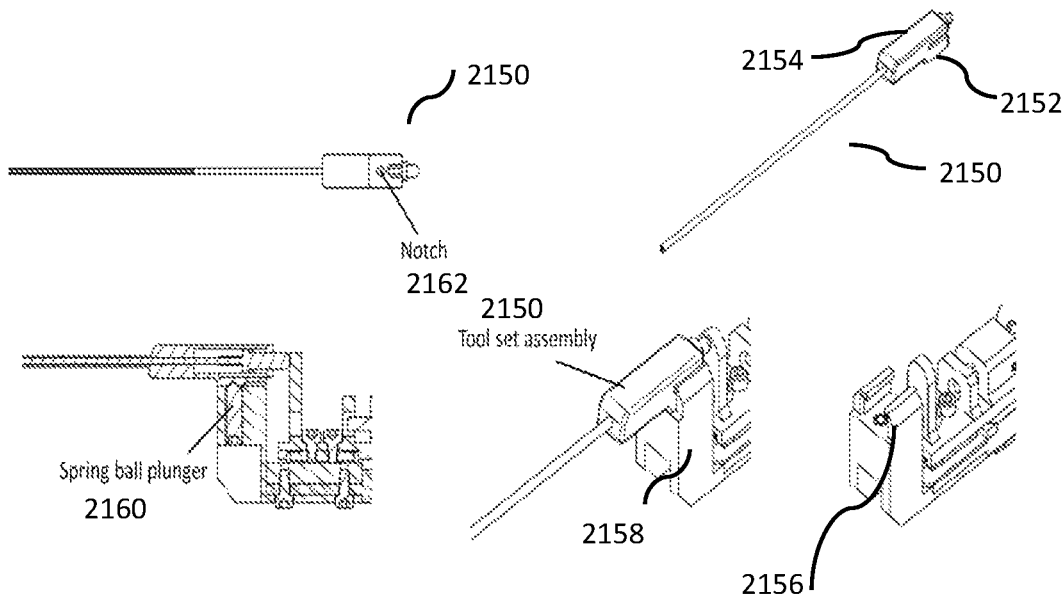

Interface Between the Toolset and Reusable Part, According to Example Embodiments For quick mounting and removing the toolset, some designs for the interface between the toolset and reusable part are shown in FIGS. 21(*a*) and (*b*).

In FIG. 21(*a*), an interface for a push-and-lock mechanism of a tool set is shown, according to an example embodiment. In this embodiment, a spring-loaded push button 2102 is located on one side of the mounting platform 2104. The push button 2102 is mechanically connected to a lock fixture 2106 on the other side of the platform 2104. When the push button 2102 is pressed, the lock fixture 2106 is slightly displaced and opened to allow the tool set 2108 to be inserted to the platform 2104. The tool set 2108 comprises four ledges e.g. 2110, one on each plane surface of a base 2111, to allow the tool set 2108 to be fittingly slid into the rail guide 2112 on the mounting platform 2104 in the desired orientation. Releasing the push button 2102 will then lock and secure the base 2111 and hence the tool set 2108. The symmetrical design of the tool set 2108 enables cutter and pusher to be rotated to particular orientation to increase the usability of the device.

Another example embodiment of an interface for a quick mounting mechanism of a tool set is shown in FIG. 21(*b*). In this plug-and-pull embodiment, the tool set 2150 comprises two guides e.g. 2152, one on each side of a base 2154, that serve to be slid into a rail guide 2156 on a mounting platform 2158. At the center of the mounting platform 2158, there is a spring ball plunger 2160 that secures the tool set 2150 by snap-fitting the notch 2162 on the base 2154. The tool set 2150 can be removed by pulling the tool set base 2154 out of the rail guide 2156.

In one embodiment of the present invention described herein, a device for incision and insertion of a ventilation tube is provided, the device comprising a cutter member configured to make an incision; a holder member configured to dispose the ventilation tube in an orientation in which a longitudinal axis of the ventilation tube is substantially perpendicular to the cutter element; and a pusher member configured to apply a pushing force to a first end of the ventilation tube in a direction substantially perpendicular to the longitudinal axis, the first end of the ventilation tube being disposed closer to the blade than a second end of the ventilation tube; wherein the holder member comprises a pivot element configured to releasably engage the second end of the ventilation tube such that the ventilation tube is pivotable about the pivot element under the pushing force applied to the first end of the ventilation tube by the pusher member, for insertion of the first end of the ventilation tube into the incision.

The device may further comprise a shaft assembly comprising a first shaft member coupled to the holder member, and a second shaft member coupled to the pusher member, wherein the first and second shaft members are moveable relative to each other. The first shaft member may be further coupled to the cutter member. The first shaft member may be coupled to the cutter member such that the first shaft member is disposed in a plane of the cutter member. The first shaft member may be coupled to the cutter member such that the first shaft member is disposed at a non-zero angle relative to a plane of the cutter member. The first shaft member may comprise a curved tip element coupled to the cutter member.

The shaft assembly may further comprise a third shaft member coupled to the cutter member moveable relative to the first and second shaft members. The third shaft member may be configured to be retractable in a direction away from the incision prior to the pusher member applying the pushing force to the first end of the ventilation tube.

The cutter member may comprise one of a group consisting of a straight cutter, a tilted cutter, a crescentic cutter, a two-step/multi-step cutter, a horizontal cutter, and a bevel cutter.

The pivot element may comprise a hook. The hook may comprise a chamfered tip or curved thin strands.

The pusher member may comprise one of a group consisting of a solid pusher with a tip having desired curvature, a pusher rod with a head element having a width larger than the pusher rod, a hollow pusher rod, a pusher rod with a long slope tip element, and a pusher rod with curved tip element.

The device may further comprise a sensor member for sensing a proximity of the cutter member to a membrane on which the incision is to be made. The sensor member may comprise a pressure sensor coupled to the cutter member. The sensor member may comprise a first deflection element configured to protrude the cutter member in a direction towards the membrane and to deflect upon contact with the membrane. The first deflection element may comprise a hair-like structure or fiber.

The device may further comprise a detector member for detecting a depth of the incision. The detector member may comprise one or more markers on the cutter member. The detector member may comprise a second deflection element configured to protrude the cutter member in a sideways direction and to deflect upon contact with the membrane. The second deflection element may comprise a hair-like structure or fiber or a pair of hair-like structures or fibers configured to protrude the cutter member in opposing sideways directions.

The device may further comprise an activation structure configured for activating movement of the pusher member for applying the pushing force to the first end of the ventilation tube. The activation structure may be further configured for activating movement of the cutter member for making the incision. The activation structure may be configured as an automatic operation structure, semi-automatic operation structure, or manual operation structure. The activation structure may be configured as a re-usable part of the device configured to cooperate with a disposable part of the device, the disposable part comprising at least the cutter member, the holder member and the pusher member.

In another embodiment of the present invention described herein, there is provided use of the device of the above embodiments in making an incision and inserting a ventilation tube in a membrane.

Figure 22:
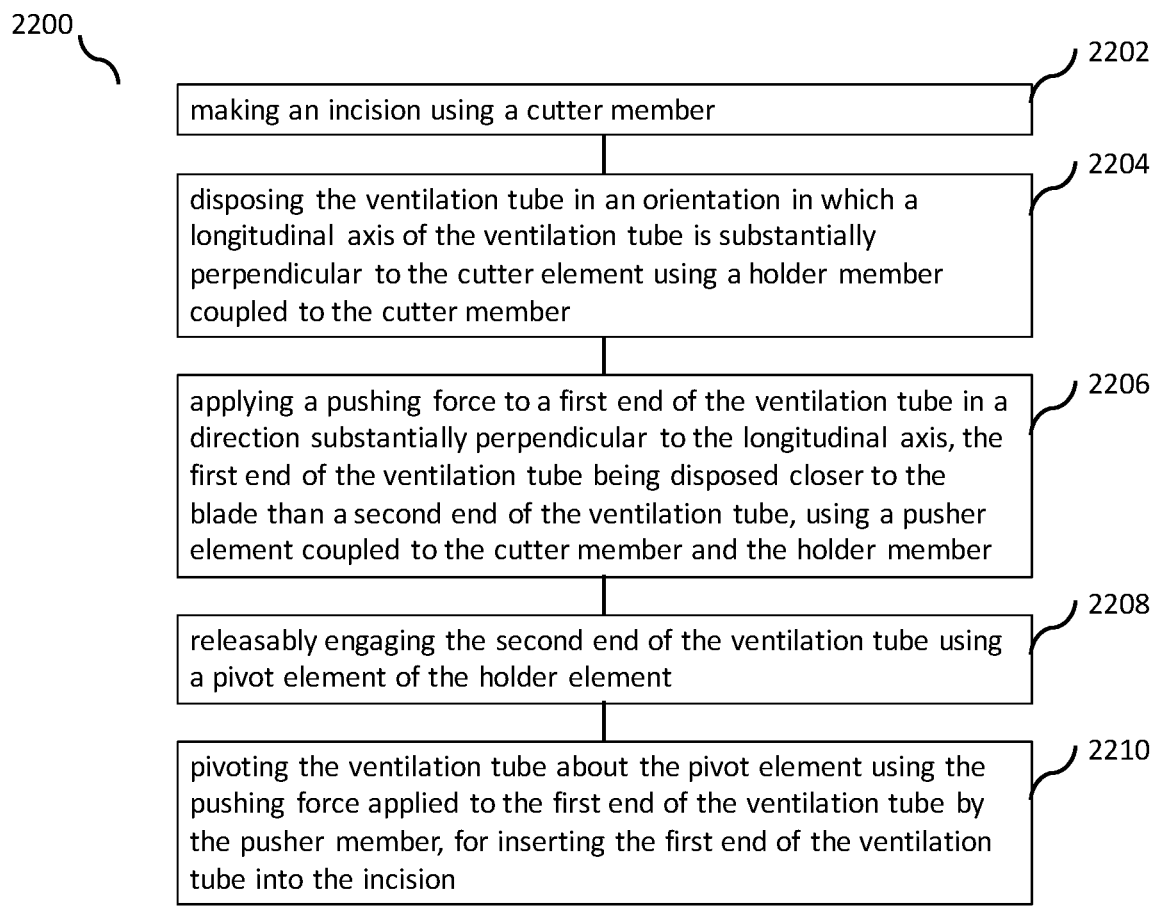
FIG. 22 shows a flowchart 2200 illustrating a method for making and incision and inserting a ventilation tube in a membrane, according to an example embodiment.

FIG. 22 shows a flowchart 2200 illustrating a method for making and incision and inserting a ventilation tube in a membrane, according to an example embodiment. At step 2202, an incision is made using a cutter member. At step 2204, the ventilation tube is disposed in an orientation in which a longitudinal axis of the ventilation tube is substantially perpendicular to the cutter element using a holder member coupled to the cutter member. At step 2206, a pushing force is applied to a first end of the ventilation tube in a direction substantially perpendicular to the longitudinal axis, the first end of the ventilation tube being disposed closer to the blade than a second end of the ventilation tube, using a pusher element coupled to the cutter member and the holder member. At step 2208, the second end of the ventilation tube is releasably engaged using a pivot element of the holder element. At step 2210, the ventilation tube is pivoted about the pivot element using the pushing force applied to the first end of the ventilation tube by the pusher member, for inserting the first end of the ventilation tube into the incision.

The above description of illustrated embodiments of the systems and methods is not intended to be exhaustive or to limit the systems and methods to the precise forms disclosed. While specific embodiments of, and examples for, the systems components and methods are described herein for illustrative purposes, various equivalent modifications are possible within the scope of the systems, components and methods, as those skilled in the relevant art will recognize. The teachings of the systems and methods provided herein can be applied to other processing systems and methods, not only for the systems and methods described above.

The elements and acts of the various embodiments described above can be combined to provide further embodiments. These and other changes can be made to the systems and methods in light of the above detailed description.

In general, in the following claims, the terms used should not be construed to limit the systems and methods to the specific embodiments disclosed in the specification and the claims, but should be construed to include all processing systems that operate under the claims. Accordingly, the systems and methods are not limited by the disclosure, but instead the scope of the systems and methods is to be determined entirely by the claims.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The invention claimed is:

1. A device for incision and insertion of a ventilation tube, the device comprising:
   a cutter member configured to make an incision;
   a holder member configured to dispose the ventilation tube in an orientation in which a longitudinal axis of the ventilation tube is substantially perpendicular to the cutter element; and
   a pusher member configured to apply a pushing force to a first end of the ventilation tube in a direction substantially perpendicular to the longitudinal axis, the first end of the ventilation tube being disposed closer to the blade than a second end of the ventilation tube;
   wherein the holder member comprises a pivot element configured to releasably engage the second end of the ventilation tube such that the ventilation tube is pivotable about the pivot element under the pushing force applied to the first end of the ventilation tube by the pusher member, for insertion of the first end of the ventilation tube into the incision.

2. The device of claim 1, further comprising a shaft assembly comprising a first shaft member coupled to the holder member, and a second shaft member coupled to the pusher member, wherein the first and second shaft members are moveable relative to each other.

3. The device of claim 2, wherein the first shaft member is further coupled to the cutter member, wherein the first shaft member is coupled to the cutter member such that the first shaft member is at least one selected from a group consisting of disposed in a plane of the cutter member and disposed at a non-zero angle relative to a plane of the cutter member.

4. The device of claim 2, wherein the shaft assembly further comprises a third shaft member coupled to the cutter member moveable relative to the first and second shaft members.

5. The device of claim 4, wherein the third shaft member is configured to be retractable in a direction away from the incision prior to the pusher member applying the pushing force to the first end of the ventilation tube, wherein the cutter member includes at least one selected from a group consisting of a straight cutter, a tilted cutter, a crescentic cutter, a two-step/multi-step cutter, a horizontal cutter, and a bevel cutter.

6. The device of claim 1, wherein the pivot element comprises a hook, the hook including a chamfered tip or curved thin strands.

7. The device of claim 1, wherein the pusher member includes at least one selected from a group consisting of a solid pusher with a tip having desired curvature, a pusher rod with a head element having a width larger than the pusher rod, a hollow pusher rod, a pusher rod with a long slope tip element, and a pusher rod with curved tip element.

8. The device of claim 1, further comprising a sensor member for sensing a proximity of the cutter member to a membrane on which the incision is to be made, wherein the sensor member includes a pressure sensor coupled to the cutter member.

9. The device of claim 8, wherein the sensor member comprises a first deflection element configured to protrude the cutter member in a direction towards the membrane and to deflect upon contact with the membrane.

10. The device of claim 9, wherein the first deflection element comprises a hair-like structure or fiber.

11. The device of claim 1, further comprising a detector member for detecting a depth of the incision.

12. The device of claim 11, wherein the detector member comprises one or more markers on the cutter member.

13. The device of claim 11, wherein the detector member comprises a second deflection element configured to protrude the cutter member in a sideways direction and to deflect upon contact with the membrane.

14. The device of claim 13, wherein the second deflection element comprises a hair-like structure or fiber or a pair of hair-like structures or fibers configured to protrude the cutter member in opposing sideways directions.

15. The device of claim 1, further comprising an activation structure configured for activating movement of the pusher member for applying the pushing force to the first end of the ventilation tube.

16. The device of claim 14, wherein the activation structure is further configured for activating movement of the cutter member for making the incision.

17. The device of claim 16, wherein the activation structure is configured as an automatic operation structure, semi-automatic operation structure, or manual operation structure.

18. The device of claim 15, wherein the activation structure is configured as a re-usable part of the device configured to cooperate with a disposable part of the device, the disposable part comprising at least the cutter member, the holder member and the pusher member.

19. The use of the device of claim 1 in making an incision and inserting a ventilation tube in a membrane.

20. A method for making and incision and inserting a ventilation tube in a membrane, the method comprising the steps of:
   making an incision using a cutter member;
   disposing the ventilation tube in an orientation in which a longitudinal axis of the ventilation tube is substantially perpendicular to the cutter element using a holder member coupled to the cutter member;
   applying a pushing force to a first end of the ventilation tube in a direction substantially perpendicular to the longitudinal axis, the first end of the ventilation tube being disposed closer to the blade than a second end of the ventilation tube, using a pusher element coupled to the cutter member and the holder member;
   releasably engaging the second end of the ventilation tube using a pivot element of the holder element; and
   pivoting the ventilation tube about the pivot element using the pushing force applied to the first end of the ventilation tube by the pusher member, for inserting the first end of the ventilation tube into the incision.

21. The device of claim 2, wherein the first shaft member comprises a curved tip element coupled to the cutter member.

* * * * *